United States Patent [19]

Lang et al.

[11] Patent Number: 4,952,391
[45] Date of Patent: Aug. 28, 1990

[54] TERT-BUTYL DERIVATIVES OF BENZYLIDENECAMPHOR, PROCESS FOR PREPARING THEM, THEIR USE AS ANTIOXIDANT AGENTS AND COSMETIC AND PHARMACEUTICAL COMPOSITIONS CONTAINING THEM

[75] Inventors: Gerard Lang, Saint-Gratien; Serge Forestter, Claye-Souilly; Alain LaGrange, Chatou; Claudine Moire, Romainville; Andre DeFlandre, Orray-la-Ville, all of France

[73] Assignee: L'Oreal, Paris, France

[21] Appl. No.: 253,970

[22] Filed: Oct. 5, 1988

[30] Foreign Application Priority Data

Oct. 5, 1987 [LU] Luxembourg ............................. 87008

[51] Int. Cl.$^5$ ............................................. A61L 9/04
[52] U.S. Cl. ......................................... 424/45; 424/59; 424/70; 514/681; 252/405; 568/327
[58] Field of Search ............... 568/327, 325, 333, 784; 424/59, 45, 70; 514/681; 252/405

[56] References Cited

U.S. PATENT DOCUMENTS

| | | | |
|---|---|---|---|
| 3,394,020 | 7/1968 | Bell et al. | 568/784 |
| 3,660,505 | 5/1972 | Starnes | 568/784 |
| 4,288,631 | 9/1981 | Ching | 568/333 |
| 4,290,974 | 9/1981 | Bouillon et al. | 568/327 |
| 4,323,549 | 4/1982 | Bouillon et al. | 424/59 |
| 4,421,739 | 12/1983 | Bouillon et al. | 568/327 |
| 4,710,584 | 12/1987 | Lang et al. | 568/327 |

*Primary Examiner*—James H. Reamer
*Attorney, Agent, or Firm*—Marshall, O'Toole, Gerstein, Murray & Bicknell

[57] ABSTRACT

New tert-butyl derivatives of benzylidenecamphor, process for preparing them, their use as antioxidant agents and cosmetic and pharmaceutical compositions containing them.

The invention relates to benzylidenecamphor derivatives of formula:

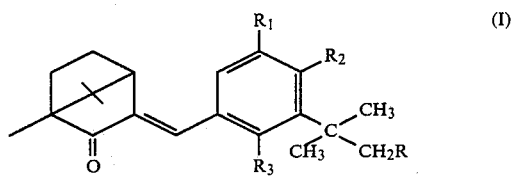

(I)

where R is hydrogen or a tert-butyl residue, $R_1$ is a $C_1$–$C_8$ alkyl or alkoxy residue, and $R_2$ and $R_3$ denote hydrogen or hydroxyl, at least one of the two being hydroxyl, to a process for preparing them and to their uses as antioxidants, broad-band sunscreens and medicinal products for the preventive treatment of skin allergies and inflammations as well as for the prevention of certain cancers.

13 Claims, No Drawings

TERT-BUTYL DERIVATIVES OF BENZYLIDENECAMPHOR, PROCESS FOR PREPARING THEM, THEIR USE AS ANTIOXIDANT AGENTS AND COSMETIC AND PHARMACEUTICAL COMPOSITIONS CONTAINING THEM

The present invention relates to new tert-butyl derivatives of benzylidenecamphor, to a process for preparing them and to their uses as antioxidant agents as well as in cosmetic compositions for daily use or for protection against sunlight and in pharmaceutical compositions for the preventive treatment of skin allergies and inflammations or certain forms of cancer.

It is well known that the skin is sensitive to solar radiation, which can cause ordinary sunburn or erythema, but also more or less pronounced burns.

However, solar radiation also has other deleterious effects, such as a loss of elasticity of the skin and the appearance of wrinkles leading to premature aging. Sometimes, even dermatoses can also be observed. The extreme case is the occurrence of skin cancers in some subjects.

It is also desirable to provide the hair with good protection against photochemical degradation, in order to avoid a change in hue, a bleaching or a degradation of the mechanical properties.

It is known, moreover, that the constituents participating in cosmetic preparations do not always possess sufficient light-fastness, and are degraded through the action of light radiation.

It is well known that the most dangerous portion of solar radiation consists of ultraviolet radiation of wavelengths less than 400 nm. It is also known that, as a result of the existence of the ozone layer of the earth's atmosphere, which absorbs a portion of the solar radiation, the lower limit of ultraviolet radiation reaching the earth's surface lies at about 280 nm.

Accordingly, it appears desirable to have recourse to compounds capable of absorbing ultraviolet radiation over a wide band of wavelengths ranging from 280 to 400 nm, that is to say both the UV-B rays of wavelengths between 280 and 320 nm that play a predominant part in the production of solar erythema, and the UV-A rays of wavelengths between 320 and 400 nm that cause tanning of the skin but also its aging, and that promote the triggering of the erythemal reaction or that augment that reaction in some subjects or that can even be the source of phototoxic or photoallergic reactions.

In the course of their investigations, applicants have discovered new benzylidenecamphor derivatives having the following formula:

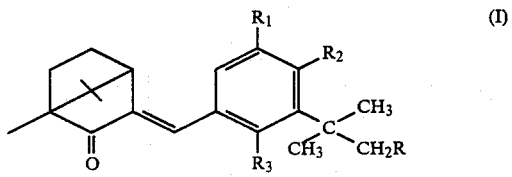

in which:
R denotes a hydrogen atom or a tert-butyl residue,
$R_1$ denotes a $C_1$–$C_8$ linear or branched alkyl residue or a $C_1$–$C_8$ linear or branched alkoxy residue, and
$R_2$ and $R_3$ denote a hydrogen atom or a hydroxyl radical, with the proviso that at least one of the radicals $R_2$ and $R_3$ denotes a hydroxyl radical.

Apart from their good screening properties in the wavelength range extending from 280 to 380 nm, the above compounds simultaneously exhibit, unexpectedly, excellent antioxidant properties with respect to the peroxidation of polyunsaturated lipids, and also with respect to substances capable of undergoing thermo- or photoinduced oxidation reactions (such as proteins, polymers, etc.).

Now, it is known that the peroxidation of lipids involves the formation of intermediate free radicals which damage cell membranes composed, inter alia, of phospholipids, and are responsible, in particular, for phenomena of aging of the skin (A. L. Tappel in "Federation Proceedings" Vol. 32, No. 8, August 1973).

It is extremely advantageous to have recourse to compounds exhibiting both screening properties over a wide band and antioxidant properties boosting the screening effect. Such compounds can make it possible, for example, to combat more satisfactorily the premature aging of the skin due to the peroxidation of cutaneous lipids.

They can also make it possible to provide for better preservation of cosmetic compositions containing a fatty phase, by preventing the rancidification of the unsaturated lipids present therein, and which can be of animal origin, such as lanolin, cetin (spermaceti), beeswax, perhydrosqualene or turtle oil, or vegetable origin such as olive oil, castor oil, maize oil, sweet almond oil, avocado oil, shea oil, sunflower oil, soybean oil, groundnut oil or hydrogenated coconut or palm-kernel oils, and of essential fatty acids such as vitamin F and certain essential oils present in perfumes such as lemon or lavender oil.

Applicants also discovered, extremely surprisingly, that the compounds of formula (I) above could be used for the preventive treatment of skin allergies and inflammations and also in the prevention of certain cancers.

Apart from their good screening and antioxidant properties, the compounds according to the invention possess an excellent lipid-soluble nature as well as very good thermal and photochemical stability.

These compounds also have the advantage of not being toxic or irritant and of being completely safe with respect to the skin.

They distribute uniformly in traditional cosmetic vehicles capable of forming a continuous film and, in particular, in fatty vehicles, and can thus be applied on the skin to form an effective protective film.

The subject of the present invention is hence the compounds of formula (I) above.

In this formula, $R_1$ can denote, for example, a methyl, ethyl, n-propyl, isopropyl, n-butyl, isobutyl, tert-butyl or 1,1,3,3-tetramethylbutyl radical or alternatively a methoxy, ethoxy, propoxy, butoxy, pentyloxy, hexyloxy, heptyloxy or octyloxy residue.

Among preferred compounds of general formula (I), there may be mentioned:
3'-tert-butyl-2'-hydroxy-5'-methoxy-3-benzylidene-dl-camphor,
3'-tert-butyl-2'-hydroxy-5'-methyl-3-benzylidene-dl-camphor,
3',5'-di-tert-butyl-4'-hydroxy-3-benzylidene-dl-camphor,
3',5'-di-tert-butyl-2'-hydroxy-3-benzylidene-dl-camphor, and 3'-tert-octyl-2'-hydroxy-5 -methyl-3-benzylidene-dl-camphor.

The compounds of formula (I) are obtained from synthetic camphor (dl-camphor) or from natural camphor (d-camphor) by condensation with an aromatic aldehyde of formula:

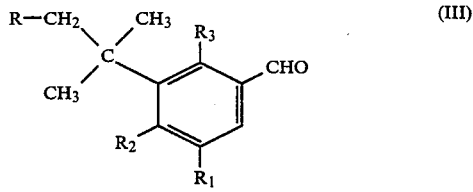

R, $R_1$, $R_2$ and $R_3$ having the meanings stated above.

The aldehydes of formula (III) are prepared according to known methods.

The condensation of the aldehyde (III) with camphor may be performed according to one of the following two processes:

1st PROCESS

The condensation is performed in the presence of an alkali metal alcoholate such as sodium methylate or potassium tert-butylate, in a solvent such as toluene, at the reflux temperature of the solvent.

The condensation can also be performed in the presence of an inorganic base such as an alkali metal amide or hydride, in the presence of a solvent such as dimethoxyethane, at the reflux temperature of the solvent.

2nd PROCESS

The condensation of the aldehyde (III) with camphor is performed in the presence of a borane of the following formula (IV):

in which $R_4$ denotes a $C_1-C_6$ alkyl residue and $R_5$ denotes $C_1-C_4$ alkyl residue. This compound is obtained according to the procedure described by L. H. Toporcer et al., J. Am. Chem. Soc. 87, 1236 (1965). Its isolation and purification are not necessary in order to carry out the condensation of the aldehyde (III) with camphor.

The condensation reaction is performed at a temperature of 140°–160° C. without a solvent.

The subject of the present invention is hence also the process for preparing the new compounds of formula (I).

Another subject of the invention is a cosmetic composition comprising an effective amount of at least one benzylidenecamphor derivative of formula (I) above, in a cosmetically acceptable vehicle containing at least one fatty phase.

The cosmetic composition of the invention may be used as a composition for protecting the human epidermis or the hair or as an antisun composition.

The subject of the present invention is also a process for protecting the skin and natural or sensitized hair with respect to solar radiation, consisting in applying on the skin or hair an effective amount of at least one compound of formula (I) contained in a cosmetically acceptable vehicle containing at least one fatty phase.

"Sensitized hair" is understood to mean hair which has undergone a permanent-waving, dyeing or bleaching treatment.

The subject of the invention is also a coloured or uncoloured cosmetic composition, stabilized to light and/or oxidation, comprising an effective amount of at least one benzylidenecamphor derivative of formula (I) above.

When used as a composition intended for protecting the human epidermis against ultraviolet rays, the cosmetic composition according to the invention may be presented in the most diverse forms customarily used for this type of composition. It can, in particular, be presented in the form of oily or oleoalcoholic lotions, of emulsions such as a cream or a milk, of oleoalcoholic, alcoholic or aqueous-alcoholic gels, or of solid sticks, or be packaged as an aerosol.

It can contain cosmetic adjuvants customarily used in this type of composition, such as thickeners, emollients, humectants, surfactants, preservatives, antifoams, perfumes, oils, waxes, lanolin, propellants, colourings and/or pigments whose function is to colour the composition itself or the skin, or any other ingredient customarily used in cosmetics.

The compound of formula (I) is present in proportions by weight of between 0.1 and 2% relative to the total weight of the cosmetic composition for protecting the human epidermis.

As a solubilization solvent, it is possible to use an oil, a wax and, generally speaking, any fat, a monohydric alcohol or a lower polyol or mixtures thereof. More especially preferred monohydric alcohols or polyols are ethanol, isopropanol, propylene glycol, glycerin and sorbitol.

One embodiment of the invention is an emulsion in the form of a protective cream or milk comprising, in addition to the compound of formula (I), fatty alcohols, fatty acid esters and, in particular, fatty acid triglycerides, fatty acids, lanolin, natural or synthetic oils or waxes, and emulsifiers, in the presence of water.

Another embodiment consists of oily lotions based on natural or synthetic oils and waxes, lanolin and fatty acid esters, in particular fatty acid triglycerides, or of oleoalcoholic lotions based on a lower alcohol such as ethanol or a glycol such as propylene glycol and/or a polyol such as glycerin, and oils, waxes and fatty acid esters such as fatty acid triglycerides.

The cosmetic composition of the invention can also be an alcoholic gel comprising one or more lower polyols or alcohols such as ethanol, propylene glycol or glycerin, and a thickener such as silica. The oleoalcoholic gels contain, in addition, a natural or synthetic oil or wax.

The solid sticks consist of natural or synthetic oils and waxes, fatty alcohols, fatty acid esters, lanolin and other fats.

The present invention also relates to the antisun cosmetic compositions containing at least one compound of formula (I) and capable of containing other UV-B and/or UV-A screening compounds.

In this case, the amount of compound of formula (I) is between 0.2 and 15% by weight. The total amount of screening compounds present in the antisun composition, that is to say the compound of formula (I) and, where appropriate, the other screening compounds, being between 0.5 and 15% by weight relative to the total weight of the antisun composition.

In the case of a composition packaged as an aerosol, traditional propellants are used, such as alkanes, fluoroalkanes and chlorofluoroalkanes.

When the cosmetic composition according to the invention is intended for protecting natural or sensitized hair from UV rays, this composition may be presented in the form of a shampoo, a lotion, gel or emulsion to be rinsed, to be applied before or after shampooing, before or after dyeing or bleaching, or before or after permanent-waving, a styling or treating lotion or gel, a lotion or gel for blow-drying or setting, a hair lacquer, or a composition for permanent-waving, dyeing or bleaching the hair. This composition can contain, apart from the compound of the invention, various adjuvants used in this type of composition, such as surfactant agents, thickeners, polymers, emollients, preservatives, foam stabilizers, electrolytes, organic solvents, silicone derivatives, oils, waxes, antigrease agents, colourings and/or pigments whose function is to colour the composition itself or the hair, or any other ingredient customarily used in the hair-care field.

It contains 0.25 to 2% by weight of compound of formula (I).

The present invention also relates to the cosmetic compositions containing at least one compound of formula (I) by way of an agent for protection against ultraviolet rays and an antioxidant agent, consisting of hair-care compositions such as hair lacquers, hair-setting lotions optionally having treating or disentangling properties, shampoos, colouring shampoos and hair dyeing compositions, and of makeup products such as nail varnishes, treatment creams and oils for the epidermis, makeup foundations, lipsticks and skin care compositions such as bath oils or creams, as well as any other cosmetic composition capable of exhibiting, as a result of its constituents, problems of light-fastness and/or stability to oxidation during storage.

Such compositions contain 0.1 to 2% by weight of compound of formula (I).

The invention also relates to a process for protecting cosmetic compositions against ultraviolet rays and oxidation, consisting in incorporating an effective amount of at least one compound of formula (I) in these compositions Another subject of the invention is the use of the compounds of formula (I) as antioxidant agents.

Another subject of the invention is the use of the compounds of formula (I) as broad-band sunscreen absorbing in the wavelength range extending from 280 to 380 nm.

The subject of the invention is also the application of the compounds of formula (I) by way of cosmetic products.

As stated above, the Applicant discovered, in addition, in the course of his investigations, that the compounds of formula (I) exhibited advantageous pharmacological activity in the field of the preventive treatment of skin allergies and inflammations, and could also be used in the prevention of certain cancers.

The subject of the invention is hence the compound of formula (I), in respect of its use as a medicinal product.

The subject of the invention is also a pharmaceutical composition containing an effective amount of at least one compound of formula (I) by way of an active ingredient, in a non-toxic excipient or vehicle.

The pharmaceutical composition according to the invention may be administered orally or topically.

For oral administration, the pharmaceutical composition may be presented in the form of tablets, hard gelatin capsules, dragees, syrups, suspensions, solutions, emulsions, and the like. For topical administration, the pharmaceutical composition according to the invention is presented in the form of an ointment, cream, pomade, solution, lotion, gel, spray, suspension and the like.

This medicinal composition can contain inert or pharmacodynamically active additives, and in particular: moisturizing agents, antibiotics, steroidal or non-steroidal anti-inflammatory agents, carotenoids and antipsoriatic agents.

This composition can also contain flavour-improving agents, preservative agents, stabilizing agents, moisture-regulating agents, pH-regulating agents, osmotic pressure-modifying agents, emulsifying agents, local anaesthetics, buffers, and the like.

It can also be packaged in delay or sustained-release forms which are known per se.

The compound of formula (I) according to the invention is present in the pharmaceutical compositions in proportions of between 0.01 and 80% by weight relative to the total weight of the composition, and preferably between 0.1 and 20% by weight.

In the therapeutic application, the treatment is determined by the doctor and can vary according to the patient's age, weight and response, as well as the severity of the symptoms.

When the compounds of formula (I) are administered orally, the dosage is generally between 0.1 and 50 mg/kg/day, and preferably between 0.2 and 20 mg/kg/day. The treatment period is variable, depending on the severity of the symptoms, and can extend between 1 and 25 weeks, continuously or discontinuously.

The compositions for topical administration preferably contain from 0.25% to 4% by weight of compound of formula (I).

As vehicle or excipient for the pharmaceutical composition of the invention, all non-toxic conventional vehicles or excipients may be used.

The examples which follow are designed to illustrate the invention without a limitation of the latter being implied.

PREPARATION EXAMPLES

EXAMPLE 1

Preparation of 3'-tert-butyl-2'-hydroxy-5'-methoxy-3-benzylidene-dl-camphor of formula

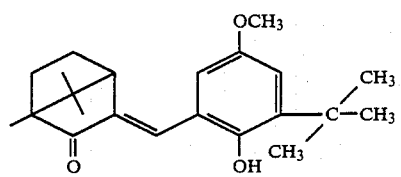

21 g (0.138 mol) of dl-camphor are dissolved in 100 cm³ of dimethoxyethane dried over a 4 Å molecular sieve. 6.35 g (0.276 mol) of sodium hydride are added and the mixture is heated under reflux for one hour.

24 g (0.115 mol) of 3-tert-butyl-2-hydroxy-5-methoxybenzaldehyde, dissolved in 80 cm³ of 1,2-dimethoxyethane, are added dropwise The mixture is heated under reflux for 3 hours. After being cooled, the reaction mixture is poured into water. The mixture is acidified by adding 10% strength hydrochloric acid. The precipitate formed is filtered off, washed with water and recrystallized in absolute ethanol.

12.35 g (31%) of expected product are obtained, possessing the following characteristics:
appearance: yellow crystals
melting point: 223° C.
elemental analysis: $C_{22}H_{30}O_3$

|  | C % | H % | O % |
| --- | --- | --- | --- |
| Calculated | 77.15 | 8.83 | 14.01 |
| Found | 76.87 | 8.83 | 13.88 |

UV spectrum (methanol): $\lambda\ max_1 = 297$ nm $\epsilon = 15700$, $\lambda max_2 = 365$ nm $\epsilon = 10460$.

$^1$H NMR Spectrum (80 MHz) (CDCl$_3$+DMSO-d$_6$): in agreement with the expected structure.

EXAMPLE 2

Preparation of 3'-tert-butyl-2'-hydroxy-5'-methyl-3-benzylidene-dl-camphor

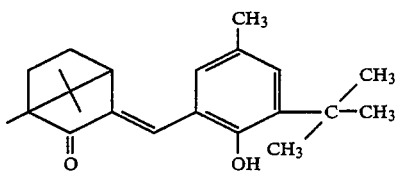

This compound is obtained according to the procedure described in Example 1, in which 3-tert-butyl-2-hydroxy-5-methoxybenzaldehyde is replaced by 3-tert-butyl-2-hydroxy-5-methylbenzaldehyde.

The product obtained possesses the following characteristics:
appearance: yellow crystals
melting point: 213° C.
elemental analysis: $C_{22}H_{30}O_2$

|  | C % | H % | O % |
| --- | --- | --- | --- |
| Calculated | 81.18 | 8.98 | 9.83 |
| Found | 81.39 | 9.04 | 9.92 |

UV spectrum (methanol) $\lambda\ max_1 = 295$ nm $\epsilon = 14600$, $\lambda\ max_2 = 335$ nm $\epsilon = 8470$.

$^1$H NMR Spectrum (80 MHz) (CDCl$_3$+DMSO-d$_6$): in agreement with the expected structure.

EXAMPLE 3

Preparation of 3',5'-di-tert-butyl-4'-hydroxy-3-benzylidenecamphor

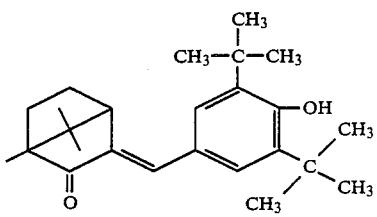

(a) 1st method of synthesis: (derived from natural camphor)

50 (0.328 mol) of d-camphor are dissolved in 400 cm$^3$ of 1,2-dimethoxyethane. 17.5 g of sodium hydride (0.73 mol) are added and the mixture is brought to reflux for one hour. 70 g (0.3 mol) of 3,5-di-tert-butyl-4-hydroxybenzaldehyde are added and the mixture is heated under reflux for 10 hours. After being cooled, the reaction medium is gradually diluted with 100 cm$^3$ of ethanol and then with 100 cm$^3$ of water. The mixture is acidified by adding 10% strength hydrochloric acid. The precipitate formed is filtered off, washed with water and dried. After recrystallization in isopropyl ether and then in ethanol, 54.5 g (49% yield) of expected product are obtained, possessing the following characteristics:
appearance: white crystals
melting point: 186° C.
elemental analysis $C_{25}H_{36}O_2$

|  | C % | H % | O % |
| --- | --- | --- | --- |
| Calculated | 81.47 | 9.84 | 8.68 |
| Found | 81.40 | 9.87 | 8.79 |

UV spectrum (chloroform) $\lambda max$: 325 nm $\epsilon = 23000$.
$^1$H NMR Spectrum (80 MHz) (CDCl$_3$+DMSO-d$_s$): in agreement with the expected structure.

(b) 2nd method of synthesis: (derived from synthetic camphor)

41 g (0.4 mol) of pivalic acid are added at 0° C. to 500 cm$^3$ of a 1M solution of triethylborane in hexane. After 15 min of stirring at 0° C., the mixture is allowed to return to room temperature, and 28 g (0.19 mol) of di-camphor and 44.5 g (0.19 mol) of 3,5-di-tert-butyl-4-hydroxybenzaldehyde are then added.

The hexane is distilled off and the mixture is heated to 150°–160° C. for 3 hours. The volatile products are distilled off under reduced pressure (1995 Pa.s, then 13 Pa.s).

The reaction mixture is diluted with 200 cm$^3$ of ethyl acetate. The organic phase is washed with water and then dried. The solvent is distilled off under reduced pressure. After recrystallization in isopropyl ether, 50.1 g (72% yield) of expected product are obtained, possessing the following characteristics:
appearance: white crystals
melting point: 158° C.
elemental analysis: $C_{25}H_{36}O_2$

|  | C % | H % | O % |
| --- | --- | --- | --- |
| Calculated | 81.47 | 9.84 | 8.68 |

-continued

| | C % | H % | O % |
|---|---|---|---|
| Found | 81.37 | 9.84 | 8.78 |

UV spectrum (chloroform) λ max=323 nm ε=24200
$^1$H NMR Spectrum (80 MHz) (CDCl$_3$+DMSO-d$_6$):
in agreement with the expected structure.

EXAMPLE 4

Preparation of
3',5'-di-tert-butyl-2,-hydroxy-3-benzylidene-dl-camphor of formula

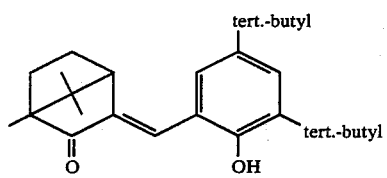

This compound is obtained according to the procedure described in Example 1, in which 3-tert-butyl-2-hydroxy-5-methoxybenzaldehyde is replaced by 3,5-di-tert-butyl-2-hydroxybenzaldehyde.

The product obtained possesses the following characteristics:
Melting point: 220° C.
Elemental analysis: C$_{25}$H$_{36}$O$_2$

| | C % | H % | O % |
|---|---|---|---|
| Calculated | 81.47 | 9.85 | 8.68 |
| Found | 81.29 | 9.79 | 8.89 |

UV spectrum (dichloromethane) λ max$_1$: 292 nm ε$_1$: 13000 λ max$_2$: 330 nm ε$_2$: 7500.
$^1$H NMR Spectrum (80 MHz) (CDCl$_3$+DMSO-d$_6$):
in agreement with the expected structure.

EXAMPLE 5

Preparation of
3'-tert-octyl-2'-hydroxy-5'-methyl-3-benzylidene-dl-camphor of formula

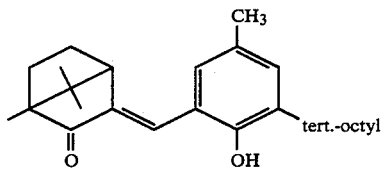

This compound is obtained according to the procedure described in Example 1, in which 3-tert-butyl-2-hydroxy-5-methoxybenzaldehyde is replaced by 3-tert-octyl-2-hydroxy-5-methylbenzaldehyde.

The product obtained possesses the following characteristics:
Melting point: 176° C.
Elemental analysis: C$_{26}$H$_{38}$O$_2$

| | C % | H % | O % |
|---|---|---|---|
| Calculated | 81.62 | 10.01 | 8.36 |
| Found | 81.84 | 9.95 | 8.51 |

UV spectrum (dichloromethane) λ max$_1$: 293 nm, ε$_1$: 12000, λ max$_2$: 335 nm, ε$_2$: 6460.
$^1$H NMR Spectrum (80 MHz) (CDCl$_3$+DMSO-d$_6$):
in agreement with the expected structure.

APPLICATION EXAMPLES

Example 1—Antisun oil

The following ingredients are mixed, optionally heating to 40°-45° C. in order to homogenize:
Compound of Example 3 0.6 g
Benzoate of C$_{12}$-C$_{15}$ alcohols, sold by
FINETEX under the name "FINSOLV TN" 30.0 g
Sunflower oil 20.0 g
Perfume 1.0 g
Cyclic dimethylpolysiloxane sold by UNION CARBIDE under the name "VOLATILE SILICONE 7207" qs 100 g The compound of Example 3 may be replaced by that of Example 4

Example 2—Gel for protecting the skin

The following gel is prepared:
Compound of Example 3 0.12 g
Polyacrylic acid crosslinked with a polyfunctional agent, sold by the company GOODRICH under the name "CARBOPOL 934" 0.8 g
Glycerin 12.0 g
Ethanol 15.0 g
Preservative 0.2 g
Perfume 0.2 g
Triethanolamine qs pH 5.3
Demineralized water qs 100 g The screening compound is dissolved in the ethanol/glycerin mixture; the water, preservative and perfume are added. In this aqueous phase, the Carbopol is dispersed homogeneously and the pH is adjusted to 5.3 with triethanolamine.

Example 3—Antisun stick

The following solid stick is prepared:
Compound of Example 3 1.0 g
Ozocerite "SP 1020"(STRAHL & PITSCH) 20.0 g
Beeswax 7.0 g
Oleyl alcohol 12.0 g
Hydrogenated lanolin "HYDROLAN H" (ONYX CHEMICAL) 8.0 g
Lanolin oil "ARGONOL 60" (WESTBROOK LANOLIN) 8.0 g
Carnauba wax 1.0 g
Benzoate of C$_{12}$-C$_{15}$ alcohols "FINSOLV TN" (FINETEX) 17.0 g
Octamethylcyclotetrasiloxane "ABIL K4" (GOLDSCHMIDT) 3.0 g
Liquid paraffin qs 100. g The various compounds are melted at about 70°-75° C. so as to obtain a liquid phase in which the screening compound is dissolved. This solution is poured into moulds and allowed to cool.

Example 4—Antisun milk

Compound of Example 3 0.25 g
Benzylidenecamphor 2.0 g
Mixture of fatty acid esters, polyglycerolated esters and silicone-based surfactants "ABIL WSO8" (GOLDSCHMIDT) 5.0 g
White vaseline 2.0 g
Beeswax 2.5 g Benzoate of $C_{12}$–$C_{15}$ alcohols "FINSOLV TN" (FINETEX) 19.0 g
Glycerin 5.0 g
Sodium chloride 2.0 g
Perfume 0.4 g
Preservative 0.2 g
Demineralized water qs 100. g This is a water-in-oil emulsion. The screening compounds are dissolved in the fat and the emulsifier and the mixture is heated to 70°–80° C.; the aqueous phase consisting of the water, sodium chloride and glycerin is heated to the same temperature; the aqueous phase is added to the fatty phase with brisk stirring, the mixture is then allowed to cool with moderate stirring and to about 40° C., and perfume and preservative are added.

Example 5—Antisun milk

Compound of Example 3 1.5 g
2-Ethylhexyl p-methoxycinnamate "PARSOL MCX" (GIVAUDAN) 3.5 g
2-Hydroxy-4-methoxybenzophenone "UVINUL M40" 1.0 g
Cetyl alcohol 1.0 g
Oleocetyl alcohol containing 30 mol of ethylene oxide "MERGITAL OC 30" (HENKEL) 5.0 g
Stearyl alcohol 4.0 g
Synthetic oil of formula:

| Compound of Example 3 | 1.5 g |
| 2-Ethylhexyl p-methoxycinnamate "PARSOL MCS" (GIVAUDAN) | 3.5 g |
| 2-Hydroxy-4-methoxybenzophenone "UVINUL M40" | 1.0 g |
| Cetyl alcohol | 1.0 g |
| Oleocetyl alcohol containing 30 mol of ethylene oxide "MERGITAL OC 30" (HENKEL) | 5.0 g |
| Stearyl alcohol | 4.0 g |
| Synthetic oil of formula: | 2.0 g |

$$C_{15}H_{31}COOCH_2-\underset{OH}{CH}-CH_2OCH_2-\underset{C_2H_5}{CH}-C_4H_9$$

90:10 Mixture of cetostearyl 2-ethylhexanoate and isopropyl myristate "CERAMOLL" (Créations Aromatiques) 2.0 g
Liquid paraffin 8.0 g
Propylene glycol 4.0 g
Preservative 0.2 g
Perfume 0.4 g
Demineralized water qs 100. g This is an oil-in-water emulsion. The screening compounds are dissolved in the fats at about 70°–80° C.; the aqueous phase consisting of the water, propylene glycol and emulsifier is heated to the same temperature, and the fatty phase is added to the aqueous phase with brisk stirring, the mixture is then allowed to cool with moderate stirring and preservative and perfume are added at about 4° C.

Example 6—Antisun cream

The following cream, forming an oil-in-water emulsion, the aqueous phase of which consists of water, sorbitol, sodium lactate and emulsifier and in which {4[(2-oxo-3-bornylidene)methyl]phenyl}trimethylammonium methylsulphate is dissolved, is prepared in the same manner as in Example 5:
Compound of Example 3 0.5 g
{4-[(2-Oxo-3-bornylidene)methyl]-phenyl}trimethylammonium methylsulphate 4.0 g
Sodium lactate, 60% pure 1.0 g
Mixture of cetyl stearyl alcohol and cetylstearyl alcohol oxyethylenated with 33 mol of ethylene oxide "SIMMOWAX AO" (HENKEL) 7.5 g
Cetyl alcohol 1.0 g
Myristyl alcohol "SIPOL C14" (HENKEL) 0.6 g
Sorbitol, 70% pure 3.0 g
Isopropyl palmitate 10.0 g
Liquid paraffin 7.0 g
Preservative 0.2 g
Perfume 0.6 g
Demineralized water qs 100. g Example 7—Antisun oil The following ingredients are mixed, optionally heating to 40°–45° C. in order to homogenize:
Compound of Example 2 0.2 g
p-Methylbenzylidenecamphor 2. g
Perfume qs
Isopropyl myristate qs 100. g The compound of Example 2 may be replaced by that of Example 5.

In Examples 8 and 9 below, the compounds of the invention are used as antioxidants in order to prevent rancidification of the compositions.

Example 8—Care cream

The following cream, forming a water-in-oil emulsion, the aqueous phase of which comprises water, ascorbic acid, EDTA, glutathione and citric acid, is prepared in the same manner as in Example 4:
Magnesium lanolate 14.4 g
Lanoline alcohol 3.6 g
Sunflower oil 40.0 g
Isopropyl myristate 8.0 g
Ozocerite 4.0 g
Vitamin F 2.0 g
Ascorbic acid 0.5 g
Soybean lecithin 5.0 g
Compound of Example 3 0.25 g
Ascorbyle palmitate 1.0 g
Glutathione 0.1 g
N-Acetylcysteine 0.05 g
Citric acid 0.05 g
Ethylenediaminetetraacetic acid (EDTA) 0.15 g
Perfume 0.8 g
Methyl para-hydroxybenzoate 0.3 g
Water qs 100. g Example 9—Face and body oil The following ingredients are mixed, optionally heating to 40°–45° C. in order to homogenize:
Shea oil 2.0 g
Sunflower oil 31.8 g
Vitamin F 2.0 g
Soybean oil 32.0 g
Compound of Example 1 0.1 g
Citric acid 0.05 g
Ascorbyl palmitate 1.0 g
N-Acetylcysteine 0.1 g
Ethylenediaminetetraacetic acid (EDTA) 0.15 g
Soybean lecithin 0.1 g
Groundnut oil qs 100. g Pharmaceutical compositions used topically Example 10—Soothing ointment (To be applied on irritated skin in order to bring relief)
Compound of Example 3 2.00 g
Fluid paraffin oil 9.10 g
Silica sold by the company DEGUSSA under the name "AEROSIL 200" 9.20 g
Isopropyl myristate qs 100. g Example 11—Anti-inflammatory (oil-in-water) cream Compound of Example 4 3.00 g
Sodium dodecyl sulphate 0.80 g
Glycerol 2.00 g
Stearyl alcohol 20.00 g
Triglycerides of capric/caprylic acids, sold by the company DYNAMIT NOBEL under the name "MIGLYOL 812" 20.00 g
Preservatives qs
Demineralized water qs 100. g Example 12—Soothing gel Compound of Example 5 1.00 g
Hydroxypropyl cellulose sold by the company HERCULES under the name "KLUCEL HF" 2.00 g
Ethanol 70.00 g
Water qs 100. g

We claim:

1. Benzylidenecamphor derivative, of the formula:

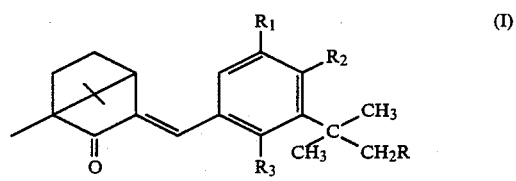

in which
R denotes a hydrogen atom or a tert-butyl residue,
$R_1$ denotes a $C_1$–$C_8$ linear or branched alkyl residue or a $C_1$–$C_8$ linear or branched alkoxy residue; and
$R_2$ and $R_3$ denote a hydrogen atom or a hydroxyl radical, with the proviso that at least one of the symbols $R_2$ and $R_3$ denotes a hydroxyl radical.

2. Compound according to claim 1, selected from the group consisting of 3'-tert-butyl-2'-hydroxy-5'-methoxy-3-benzylidene-dl-camphor, 3'-tert-butyl-2'-hydroxy-5'-methyl-3-benzylidene-dl-camphor, 3',5'-di-tert-butyl-4'-hydroxy-3-benzylidene-d-camphor, 3',5'-di-tert-butyl-4'-hydroxy-3-benzylidene-dl-camphor, 3',5'-di-tert-butyl-2'-hydroxy-3-benzylidene-dl-camphor and 3'-tert-octyl-2'-hydroxy-5'-methyl-3-benzylidene-dl-camphor.

3. Cosmetic composition, affording protection against ultraviolet radiation which comprises an effective amount of at least one compound of formula (I) according to claim 1, in a cosmetically acceptable vehicle containing at least one fatty phase.

4. Cosmetic composition according to claim 3, which comprises, by way of a compound (I), at least one of the compounds selected from the group consisting of 3'-tert-butyl-2'-hydroxy-5'-methoxy-3-benzylidene-dl-camphor, 3'-tert-butyl-2'-hydroxy-5'-methyl-3-benzylidene-dl-camphor, 3',5'-di-tert-butyl-4'-hydroxy-3-benzylidene-d-camphor, 3',5'-di-tert-butyl-4'-hydroxy-3-benzylidene-dl-camphor, 3',5'-di-tert-butyl-2'-hydroxy-3-benzylidene-dl-camphor and 3'-tert-octyl-2'-hydroxy-5'-methyl-3-benzylidene-dl-camphor.

5. Cosmetic composition according to claim 3, which is in the form of an oily or oleoalcoholic lotion, an emulsion, an oleoalcoholic, alcoholic or aqueous-alcoholic gel, a solid stick or an aerosol.

6. Cosmetic composition according to claim 5, which further contains cosmetic adjuvants selected from the group consisting of thickeners, emollients, humectants, surfactants, preservatives, antifoams, perfumes, oils, waxes, lanolin, lower polyols and monohydric alcohols, propellants, colourings and pigments.

7. Cosmetic composition according to claim 5 which constitutes a composition for protecting the human epidermis and contains 0.1 to 2% by weight of compound of formula (I).

8. Cosmetic composition according to claim 5, which is in the form of an antisun composition and contains 0.2 to 15% by weight of compound of formula (I).

9. Antisun cosmetic composition according to claim 8, which further contains an agent screening UV-B and/or UV-A rays.

10. Cosmetic composition according to claim 3 intended for application on the hair, which is in the form of a shampoo, lotion, gel or emulsion to be rinsed, styling or treating lotion or gel, lotion or gel for blow-drying or setting, hair lacquer or composition for permanent-waving, bleaching or dyeing, and comprises 0.25 to 2% by weight of compound of formula (I).

11. Cosmetic composition according to claim 3 which takes the form of a coloured or uncoloured cosmetic composition, and consists of a hair-care composition, a makeup product or a composition for skin care or treatment, comprising 0.1 to 2% by weight of compound of formula (I).

12. Process for protecting the skin and natural or sensitized hair against ultraviolet radiation, which consists in applying on the skin or hair an effective amount of a cosmetic composition containing at least one benzylidenecamphor derivative of formula (I) according to claim 1.

13. Process for protecting a cosmetic composition against ultraviolet rays and oxidation, which consists in incorporating an effective amount of at least one compound of formula (I) in this composition.

* * * * *